(12) United States Patent
Hollingsworth et al.

(10) Patent No.: US 6,288,238 B1
(45) Date of Patent: Sep. 11, 2001

(54) PROCESS FOR THE PREPARATION OF 5-HYDROXYMETHYL 2-OXAZOLIDINONE AND NOVEL INTERMEDIATE

(75) Inventors: Rawle I. Hollingsworth, Haslett, MI (US); Guijun Wang, New Haven, CT (US)

(73) Assignee: Board of Trustees operating Michigan State University, East Lansing, MI (US)

( * ) Notice: Subject to any disclaimer, the term of this patent is extended or adjusted under 35 U.S.C. 154(b) by 0 days.

(21) Appl. No.: 09/666,061

(22) Filed: Sep. 19, 2000

(51) Int. Cl.$^7$ .................................................. C07D 263/06
(52) U.S. Cl. ............................................................ 548/229
(58) Field of Search ............................................... 548/229

(56) References Cited

U.S. PATENT DOCUMENTS

| | | |
|---|---|---|
| 5,292,939 | 3/1994 | Hollingsworth . |
| 5,319,110 | 6/1994 | Hollingsworth . |
| 5,374,773 | 12/1994 | Hollingsworth . |
| 5,808,107 | 9/1998 | Hollingsworth . |

FOREIGN PATENT DOCUMENTS

62230775-A2 * 10/1987 (JP) .

OTHER PUBLICATIONS

Bartolo Gabriele et al, Organic Letters 625–627 (2000) Synthesis of 2–oxazolidinones by Direct Palladium–Catalyzed Oxidative Carbonylation.
Danielmeier, K et al., Tetrahedron–Asymmetr 6: (5) 1181–1190 (May 1995).
Warmerdam EGJC et al., Helv Chim Acta 77: (1) 252–256 (1994).
Eckert, H., et al, Angew. Chem. Int. Ed. 26: (9) 894–895 (Sep. 1987).
Seneci, P., et al, J. Chem. Soc. Perk T 1 (16) 2345–2351 (Aug. 21, 1994).
Diekema, D.J., et al., Drugs 59 7–16 (2000).
Hollingsworth, R.I. Biotechnology Annual Review 2 281–291 (1996).
Hollingsworth, R.I., J. Org. Chem. 64 7633–7634 (1999).
Wang, G., et al., J. Org. Chem. 64 1036–1038 (1999).

* cited by examiner

Primary Examiner—Floyd D. Higel
Assistant Examiner—Sonya N Wright
(74) Attorney, Agent, or Firm—Ian C. McLeod

(57) ABSTRACT

A process for preparing 5-hydroxymethyl-2-oxazolidinone (1), preferably optically active, in one step from 3,4-boronic acid ester protected 3,4-dihydroxybutyramides (2) is described. The oxazolidinone is important in the pharmaceutical industry especially in the areas of antimicrobials and behavioral disorders.

9 Claims, No Drawings

PROCESS FOR THE PREPARATION OF 5-HYDROXYMETHYL 2-OXAZOLIDINONE AND NOVEL INTERMEDIATE

CROSS-REFERENCE TO RELATED APPLICATION

None

STATEMENT REGARDING FEDERALLY SPONSORED RESEARCH OR DEVELOPMENT

None

BACKGROUND OF THE INVENTION (1) Field of the Invention

The present invention involves the preparation of 5-hydroxymethyl-2-oxazolidinone 1 from a novel cyclic boronic acid ester of 3-4-dihydroxy butyramide. The starting ester have the formula:

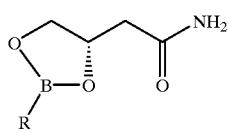

where R is a non-interfering group. The preferred oxazolidinone has the formula:

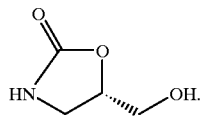

1

(2) Description of Related Art

Optically pure-5-hydroxymethyl-oxazolidinones can be obtained by carbonylation of 3-amino-1,2-dihydroxypropane (3-amino-1,2-propanediol) with reagents such as phosgene, ethyl chloroformate and carbonyl imidazole. It is also possible to perform this carbonylation reaction electrochemically. In any event, a way of preparing the optically active amino-diol has to be devised and a carbonylation step has to be performed.

General methods for the synthesis of oxazolidinones from vicinal amino alcohols:
1. Catalytic oxidation—Bartolo Gabriele, Giuseppe Salerno, Donatella Brindisi, Mirco Costa, and Gian Paolo Chiusoli, Organic Letters 625–627 (2000)—"Synthesis of 2-oxazolidinones by Direct Palladium-Catalyzed Oxidative Carbonylation of 2-Amino-1-alkanols";
2. Diethylcarbonate—Danielmeier, K.; Steckhan E.—"Efficient Pathways to (R)-5-hydroxymethyl-2-oxazolidinone and (S)-5-hydroxymethyl-2-oxazolidinone and some derivatives", Tetrahedron-Asymmetr 6: (5) 1181–1190 (May 1995);
3. Carbonyldiimidazole—Warmerdam EGJC, Brussee J., Vandergen A., Kruse, C. G., "Synthesis of (R)-5-(hydroxymethyl)-3-isopropyloxazolidin-2-one and (S)-5-(Hydroxymethyl)-3-isopropyloxazolidin-2-one, Intermediates in the preparation of optically-active beta-blockers", Helv Chim Acta 77: (1) 252—256 (1994); 4. Eckert, H., Forster, B., "Triphosgene, A crystalline phosgene substitute", Angew. Chem. Int. Ed. 26: (9) 894–895 (Sept 1987); and Seneci, P., Caspani, M., Ripamonti F., Ciabatti, R., "Synthesis and Antimicrobial Activity of Oxazolidin-2-ones and Related Heterocycles", J. Chem. Soc. Perk T 1 (16) 2345-2351 (Aug. 21, 1994).

Oxazolidinones have emerged as a very important class of compounds in drug development especially in the areas of antimicrobials (Diekema, D. J., et al., Drugs 59 7–16 (2000)) and behavioral disorders (Brenner, R., et al., Clin. Therapeut. 22 4 411–419 (2000)). They are especially active against some of the most resistant human pathogens including vancomycin-resistant enterococci, methicillin-resistant *Staphylococcus aureus*, cephalosporin-resistant *Streptococcus pneumoniae* and several organisms that display penicillin resistance (Diekema, D. J., et al., Drugs 59 7–16 (2000)). Linezolid, having the formula hereinafter, was recently recommended for approval for the treatment of infections from antibiotic resistant bacterial strains especially those that are resistant to vancomycin.

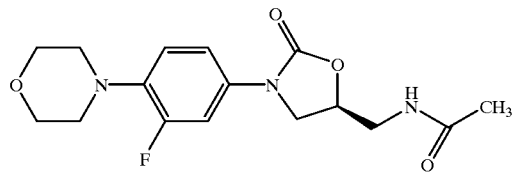

Optically active 3, 4-dihydroxybutyric acid and 3-hydroxy-y-lactones are important sources, of chirality. They can be obtained in commercial quantities from carbohydrates such as starch, lactose, maltodextrins, cellulose and arabinose by oxidative degradation (Hollingsworth, R. I. Biotechnology Annual Review 2 281–291 (1996); Hollingsworth, R. I., J. Org. Chem. 64 7633–7634 (1999)). See also U.S. Pat. Nos. 5,292,939, 5,808,107, 5,319,110 and 5,374,773 to Hollingsworth. Although 3,4-dihydroxybutramide can be readily prepared from the acids and lactones, the amides cannot be subjected directly to Hofmann reaction because of interference by the 4-hydroxyl group.

The present invention provides a way of masking and then un-masking this group. A method of doing this in which the unmasking takes place during the transformation is very valuable. This is achieved here using boronic acid esters.

SUMMARY OF THE INVENTION

The present invention relates to A process for the preparation of 5-hydroxymethyl-2-oxazolidinone which comprises:

(a) reacting a 3,4-cyclic boronic acid ester of 3,4-dihydroxy butyramide with an alkali metal or alkaline earth metal hypohalite an alkaline earth or alkali metal hydroxide to produce 5-hydroxymethyl-2-oxazolidinone;

(b) separating the 5-hydroxymethyl-2-oxazolidinone from the reaction mixture.

The present invention further relates to a process for the preparation of 5-hydroxymethyl-2-oxazolidinone which comprises:

(a) reacting in a reaction mixture 3,4-dihydroxy butyramide with a R boronic acid in a solvent, to produce a cyclic boronic acid ester, where R is an alkyl or aryl group containing 1 to 20 carbon atoms;

(b) reacting the cyclic boronic acid ester with a hypohalite and a base in an aqueous solution as a reaction mixture to produce the 5-hydroxymethyl-2-oxazolidinone; and (c) separating the 5-hydroxymethyl-2-oxazolidinone from the reaction mixture.

Other advantages of this method are that the conditions for forming boronic acid esters are not very stringent and moderate amounts of water can be tolerated. Another advantage of this method is that the carbonyl fragment of the amide is not lost during the rearrangement but is retained as the carbonyl group in the oxazolidinone ring. This is the only case in which protected dihydroxybutyramide yields oxazolidinones directly by Hofmann rearrangement. In this method a multistep process is reduced to a simple 1-pot process.

The present invention provides a method for blocking an unfavorably positioned free hydroxyl group from participating in the Hofmann and related reactions, such as the Curtius, Lossen, Beckman and Schmidt reactions where an electron-deficient nitrogen species is formed leading to rearrangements to give the products described here.

The present invention particularly provides a method for blocking a participating hydroxyl group in a Hofmann reaction such that it is de-blocked during the course of the desired transformation without the need for a separate de-blocking sequence.

OBJECTS

An object of this invention is to prepare 5-hydroxymethyl-2-oxazolidinone, such as (S)-5-hydroxymethyl-2-oxazolidinone (1), in a simple high yield from 3,4-dihydroxybutyramide without having to perform a complex protection/deprotection sequence and without having to perform a separate carbonylation step.

It is further an object of the present invention to provide a process which is economical and relatively easy to perform. These and other objects will become increasingly apparent by reference to the following description.

DESCRIPTION OF PREFERRED EMBODIMENTS

Aromatic or aliphatic boronic acid esters of optically pure 3,4-dihydroxybutyramide are transformed in a single step by Hofmann rearrangement to yield optically pure 5-hydroxymethyl-oxazolidinone directly. A protected amino-diol is not obtained as previously described for other protected 3,4-dihydroxybutyramides (Wang, G., et al., J. Org. Chem. 64 1036–1038 (1999)). A separate carbonylation reaction using phosgene, ethyl chloroformate or some similar reagent is avoided.

The new process is illustrated in Scheme 1 as follows:

Scheme 1

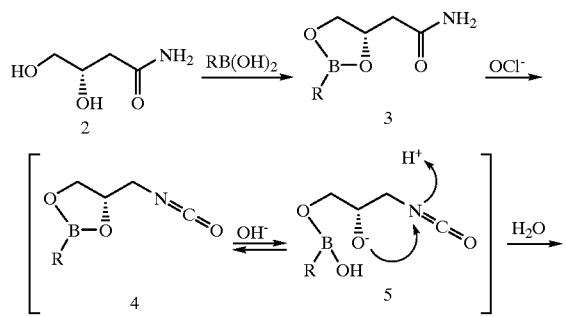

-continued

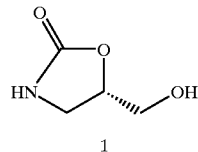

wherein R is a non-interfering group.

The process involves essentially only two steps. The first is the preparation of the boronic acid ester (3) from the dihydroxybutyramide 2. This amide is obtained in quantitative yield by treating the 3-hydroxy-y-butyrolactone with aqueous ammonia at room temperature (Wang and Hollingsworth, J. Org. Chem. 64 1036–1038 (1999)). The second step is the rearrangement of the ester under Hofmann conditions where the intermediate cyclic boronic ester isocyanate 4 goes to the ring-opened form 5 allowing the neighboring hydroxyl group to participate. A preferred 2-phase system of water and water immiscible organic solvent protects the final product from base hydrolysis. This yields the hydroxymethyl oxazolidinone 1 directly in >90% isolated yield and in >99% optical purity. This represents a tremendous economy in the synthesis of important, optically-pure 5-(hydroxymethyl)-2-oxazolidinone in essentially 3-4 steps from starch, maltose, lactose or similar 4-linked carbohydrate sources.

The alkali metal can be sodium or potassium or lithium. The alkaline earth metal can be calcium or magnesium. The hypohalite is used in an excess of preferably 2 to 6 to 1 based upon the boronic acid ester. Preferred is OCl⁻, but hypobromite can be used.

The solvent is a 2-phase water/organic system. The preferred organic solvent is tetrahydrofuran or ether dioxane, alcohol. The solvent is removed by evaporation and a volatile acid in methanol is added to remove the boric acid formed as its volatile trimethyl ester. The temperature of the reaction is between about 10° and 50° C.

The boronic acid has an R group which is preferably alkyl or aryl containing 1 to 20 carbon atoms. Other non-interfering groups can be used so long as they do not participate in reactions.

EXAMPLE

Preparation of (S)-5-Hydroxylmethyl-2-Oxazolidinone 1:

A typical procedure for the preparation and isolation: 0.5 g of the phenylboronic acid ester of 3,4-dihydroxybutyramide was dissolved in 20 ml of THF. To this solution was added 10 ml of 13% sodium hypochlorite. The mixture was left stirring at room temperature for 12 hours, after which time the rearrangement was complete as indicated by NMR spectroscopy. The reaction mixture was then concentrated and 1 ml of 2N HCl and 100 ml of methanol was added to the flask. The mixture was rotatory evaporated till dryness. This addition and removal of methanol was repeated 3 times to remove all of the boric acid. The residue was extracted with acetone several times. The extracts were combined and concentrated again to remove all solvent. The residue then was partitioned in a dichloromethane and water mixture. The water layer was concentrated to give the 5-hydroxymethyl-2-oxazolidinone as a light brown solid. Yield: 0.27 g (93.8%). The crude material can be purified by recrystallized from ethanol and dichloromethane. M.p. 89.0–90.0° C. MH⁺:118.16 ¹H NMR (300 MHz, CD₃OD) δppm: 4.70 (m, 1H), 3.76 (dd, 1 H, J=12.4, 3.6 Hz), 3.64 (m, 2 H), 3.44 (dd, J=8.7, 6.6 Hz). $^{13}$C NMR (75 MHz, CD$_3$OD), δppm: 162.4, 78.6, 63.5, 42.8. FTIR, wave number, cm$^{-1}$ 3309, 1734, 1437, 1247, 1084, 1029, 771. $\alpha^{25}_d$=38.4, ethanol, c=1.35, $\alpha^{25}_D$=48.4, methanol, c=0.5 Lit$^{20}\alpha$25$_D$= 39° ethanol, c=2.7, $\alpha^{20}_D$=48, c=1.0, methanol. The optical purity of the compound was >99.9% e.e. as determined by GC analysis of the (S)-(−)-α-Methoxy-α-(trifluoromethyl) phenylacetic acid derivatives.

It is intended that the foregoing description be only illustrative of the present invention and that the present invention be limited only by the hereinafter appended claims.

What is claimed is:

1. A process for the preparation of 5-hydroxymethyl-2-oxazolidinone which comprises:
   (a) reacting a 3,4-cyclic boronic acid ester of 3,4-dihydroxy butyramide with an alkali metal or alkaline earth metal hypohalite an alkaline earth or alkali metal hydroxide to produce 5-hydroxymethyl-2-oxazolidinone;
   (b) separating the 5-hydroxymethyl-2-oxazolidinone from the reaction mixture.

2. A process for the preparation of 5-hydroxymethyl-2-oxazolidinone which comprises:
   (a) reacting in a reaction mixture 3,4-dihydroxy butyramide with a R boronic acid in a solvent, to produce a cyclic boronic acid ester, where R is an alkyl or aryl group containing 1 to 20 carbon atoms;
   (b) reacting the cyclic boronic acid ester with a hypohalite and a base in an aqueous solution as a reaction mixture to produce the 5-hydroxymethyl-2-oxazolidinone; and
   (c) separating the 5-hydroxymethyl-2-oxazolidinone from the reaction mixture.

3. The process of claims 1 or 2 wherein the 3,4-dihydroxybutyramide and the 5-hydroxymethyl-2-oxazolidinone are optically pure.

4. The process of claim 1 wherein the alkali metal hydroxide is sodium.

5. The process of any one of claims 1 to 4 wherein the hypohalite is hypochlorite.

6. The process of any one of claims 1 to 3 wherein a volatile acid is added to the reaction mixture with methanol so that a trimethyl boric acid ester can be volatilized from the reaction mixture.

7. The process of any one of claims 1 to 3 wherein the hypohalite is in a molar ratio of 2 to 6 to 1 of the boronic acid ester.

8. The process of claims 1 to 3 wherein the alkali metal is selected from the group consisting of lithium, sodium, potassium and mixtures thereof, wherein the alkaline earth metal is selected from the group consisting of magnesium and calcium and mixtures thereof and wherein the hypohalite is selected from the group consisting of hypochlorite and hypobromite.

9. The process of any one of claims 1 to 3 conducted at a temperature between about 10° and 50° C.

* * * * *